US010744052B2

(12) United States Patent
Yamasaki et al.

(10) Patent No.: US 10,744,052 B2
(45) Date of Patent: Aug. 18, 2020

(54) TREATMENT TABLE

(71) Applicants: Masafumi Yamasaki, Kochi (JP); Kae Morita, Kochi (JP)

(72) Inventors: Masafumi Yamasaki, Kochi (JP); Kae Morita, Kochi (JP)

( * ) Notice: Subject to any disclaimer, the term of this patent is extended or adjusted under 35 U.S.C. 154(b) by 425 days.

(21) Appl. No.: 15/103,870

(22) PCT Filed: Dec. 12, 2014

(86) PCT No.: PCT/JP2014/082960
§ 371 (c)(1),
(2) Date: Jun. 12, 2016

(87) PCT Pub. No.: WO2015/087999
PCT Pub. Date: Jun. 18, 2015

(65) Prior Publication Data
US 2016/0296394 A1    Oct. 13, 2016

(30) Foreign Application Priority Data

Dec. 13, 2013 (JP) ................................. 2013/257814

(51) Int. Cl.
*A61G 7/015*    (2006.01)
*A61G 13/12*    (2006.01)
(Continued)

(52) U.S. Cl.
CPC ............ *A61G 7/015* (2013.01); *A61B 5/1116* (2013.01); *A61B 5/6892* (2013.01); *A61G 7/018* (2013.01);
(Continued)

(58) Field of Classification Search
CPC ........ A61G 7/015; A61G 7/018; A61G 13/04; A61G 13/08; A61G 13/121; A61G 13/122;
(Continued)

(56) References Cited

U.S. PATENT DOCUMENTS 1,863,236 A * 6/1932 Brienza ..................... A41H 1/02
33/427
1,940,808 A * 12/1933 Linsert ....................... F41G 1/44
33/372
(Continued)

FOREIGN PATENT DOCUMENTS

| JP | 274687 Y1 | 6/1952 |
| JP | 3512775 Y1 | 6/1960 |
| JP | 60500242 A | 2/1985 |
| JP | 2002522164 A | 7/2002 |
| JP | 2011224361 A | 11/2011 |
| WO | WO2004058124 A2 | 7/2004 |

*Primary Examiner* — Eric J Kurilla
*Assistant Examiner* — Amanda L Bailey
(74) *Attorney, Agent, or Firm* — Bayramoglu Law Offices LLC

(57) ABSTRACT

A treatment table with which it is easy to perform treatments more appropriately and which is convenient to use is provided. The treatment table includes a head support for supporting the head of a patient, a body support for supporting the body of the patient, and a waist support for supporting the waist of the patient. The head support, the body support, and the waist support are arranged in a longitudinal direction. The head support and the waist support or the body support include a swing unit capable of swing in a width direction about a central position in the width direction. Adjustment operation units for adjusting the swing units are disposed at one concentrated position of the treatment table.

3 Claims, 7 Drawing Sheets

(51) Int. Cl.
*A61B 5/11* (2006.01)
*A61G 13/08* (2006.01)
*A61B 5/00* (2006.01)
*A61G 13/04* (2006.01)
*A61G 7/018* (2006.01)
*A61G 13/10* (2006.01)

(52) U.S. Cl.
CPC .............. *A61G 13/04* (2013.01); *A61G 13/08* (2013.01); *A61G 13/121* (2013.01); *A61G 13/122* (2013.01); *A61G 13/123* (2013.01); *A61G 13/1285* (2013.01); *A61G 13/104* (2013.01)

(58) Field of Classification Search
CPC .............. A61G 13/123; A61G 13/1285; A61G 13/104; A61B 5/1116; A61B 5/6892; A61B 5/103; A61B 5/1071; A61B 2090/065; A61H 1/0222; A61H 1/001; A61H 1/003; A61H 1/0229; A61H 1/0292; A61H 1/0296; A61H 1/008; A61H 2001/0203
USPC ............ 33/785, 802; 606/587; 128/845–846; 602/32–35, 39
See application file for complete search history.

(56) References Cited

U.S. PATENT DOCUMENTS

| | | | | |
|---|---|---|---|---|
| 3,046,071 | A * | 7/1962 | Shampaine | A61G 13/02 5/608 |
| 3,411,766 | A * | 11/1968 | Lanigan | A61G 13/105 5/619 |
| 4,872,268 | A * | 10/1989 | Perrault | A61B 5/103 33/512 |
| 5,860,899 | A * | 1/1999 | Rassman | A61H 1/0222 482/131 |
| 6,421,927 | B1 * | 7/2002 | Bach | G01B 3/02 33/427 |
| 7,596,877 | B2 * | 10/2009 | Basford | G01B 3/566 33/404 |
| 2005/0044738 | A1 * | 3/2005 | Adams | G01C 9/00 33/371 |
| 2010/0211099 | A1 * | 8/2010 | Radermacher | A61G 13/009 606/245 |
| 2013/0219623 | A1 * | 8/2013 | Jackson | A61G 13/08 5/613 |
| 2013/0269710 | A1 * | 10/2013 | Hight | A61G 13/04 128/845 |

* cited by examiner

TREATMENT TABLE

TECHNICAL FIELD

The present invention relates to a treatment table used for treatments of the vertebral joints of a patient in a lying state.

BACKGROUND ART

Conventionally, as an example of this type of treatment table for treatments of vertebral joints, as disclosed in Patent Documents 1 and 2, a treatment table is known in which a head support for supporting the head of a patient, a body support for supporting the body of the patient, and a waist support for supporting the waist of the patient are arranged in a longitudinal direction, the head support is configured to be able to swing in a width direction about a point above the central position in the width direction of the head support, the body support is locked, and the waist support is configured to be able to rotate about an end of the waist support opposite the body support.

According to the conventional techniques disclosed in Patent Documents 1 and 2, since the body support is locked, the belly of a patient having a large belly becomes an obstacle and it is difficult to move the head support and the waist support to appropriate positions so as to correspond to the shape, distortion, or the like of the spine of a patient. Moreover, even when it is possible to move these head support and body support to appropriate positions, since it is not possible to move the body support from that position, it is sometimes difficult to perform an appropriate treatment.

Further, since the head support only can swing in the width direction, when the head support is swung so as to correspond to the shape, distortion, or the like of the patient's spine, it is not possible to move the waist support, following the swing of the head support. Moreover, depending on the shape, the distortion state, or the like of the patient's spine, since it is not possible to move the head support and the body support to appropriate positions, it is sometimes difficult to perform an appropriate treatment and it is not convenient to use the table.

In order to solve these problems, Patent Document 3 by the present inventors proposes a configuration in which a body mat of a treatment table body can rotate about a support point between a head support and a chest support.

The body mat is configured to be rotatable further downward so that the head support and the waist support can be moved to optimal positions so as to correspond to the position and the shape of the patient's spine while supporting a large belly of the patient on the body mat.

Moreover, in the treatment table of Patent Document 3, an inclination in the width direction of the head and the waist can be adjusted. A pair of levers is disposed on the left and right sides of each of the head support and the waist support. An operator can move the head support and the waist support so as to correspond to the shape of the patient's spine (particularly, the bending state, the distortion state, or the like) by adjusting the levers. Since the head mat of the head support and the waist mat of the waist support can be moved to more appropriate positions, it is possible to perform treatments more appropriately and improve the usability.

CITATION LIST

Patent Document

Patent Document 1: Specification of U.S. Pat. No. 4,724,828

Patent Document 2: Specification of U.S. Pat. No. 4,660,549

Patent Document 3: Japanese Patent Application Laid-Open No. 2011-224361

SUMMARY OF THE INVENTION

Problems to be Solved by the Invention

Due to provision of the treatment table of Patent Document 3, a configuration in which the chest and the body rotate in a front-rear direction is provided and it is possible to cope with the bending and the distortion in the left-right direction of the patient. On the other hand, in such a conventional configuration, it is difficult for one operator to perform adjustment so as to fit to the patient's body. Moreover, it is desirable to correct the distortion of a body and it is difficult to record changes resulting from the surgical operations. Further, treatment tables adaptable to patients of various physiques are necessary and the corresponding improvements in the treatment tables are required.

Therefore, the present invention solves the above problems of the conventional technique, and an object thereof is to provide a treatment table with which it is easy to perform treatments more appropriately and which is convenient to use.

Solution to Problems

The present invention provides the following treatment table to solve the above described problems.

That is, according to the invention of claim 1, there is provided a treatment table which includes at least a head support for supporting the head of a patient, a body support for supporting the body of the patient, and a waist support for supporting the waist of the patient and in which the head support, the body support, and the waist support are arranged in a longitudinal direction, wherein at least two supports selected from the head support, the waist support, and the body support include a swing unit capable of swing in a width direction about a central position in the width direction, and adjustment operation units for adjusting the swing units are disposed in the treatment table.

According to the invention of claim 2, there is provided a treatment table which includes at least a head support for supporting the head of a patient, a body support for supporting the body of the patient, and a waist support for supporting the waist of the patient and in which the head support, the body support, and the waist support are arranged in a longitudinal direction, wherein at least two supports selected from the head support, the waist support, and the body support include a swing unit capable of swing in a width direction about a central position in the width direction, and adjustment operation units for adjusting the swing units are disposed at one concentrated position of the treatment table.

According to the invention of claim 3, the treatment table may further include a link mechanism for connecting the swing units of the above head support and the waist support to the adjustment operation units disposed at the concentrated position.

According to the invention of claim 4, the treatment table may further include driving units for driving the swing units of the above head support and the waist support, wherein the above adjustment operation unit is configured as a switch for electrically controlling the driving unit.

According to the invention of claim 5, the treatment table may further include a sensor unit for detecting a swing position of the above swing unit; a storage unit for storing a detection value obtained by the sensor unit; and an output unit for outputting the stored detection value.

According to the invention of claim 6, the treatment table may further include a chest support for supporting the chest of the patient, wherein the head support, the chest support, the body support, and the waist support are arranged in the longitudinal direction, a length in the longitudinal direction of the body support is shorter than the length of the chest support.

According to the invention of claim 7, the above body support may be disposed at such a position that the anterior superior iliac spine of the patient is held by the body support.

According to the invention of claim 8, the central position in the width direction of the above head support may be set to a lowest point of a swing motion of the head support, and a swing range of the head support may be selected from at least one of the ranges that a displacement in a horizontal direction from the lowest point is between 30 mm and 45 mm, a displacement in a vertical direction from the lowest point is between 5 mm and 15 mm, and a rotation angle from the lowest point is between 5° and 15°. Moreover, the central position in the width direction of the above body support or the waist support may be set to a lowest point of a swing motion the body support or the waist support, and a swing range of the body support or the waist support may be selected from at least one of the ranges that a displacement in a horizontal direction from the lowest point is between 3 mm and 15 mm, a displacement in a vertical direction from the lowest point is between 20 mm and 40 mm, and a rotation angle from the lowest point is between 8° and 20°.

According to the invention of claim 9, the adjustment operation unit may be a rotation handle, and the head support may be configured to reach a maximum swing range in the width direction when the rotation handle is rotated 15 to 30 revolutions, and the body support and the waist support are configured to reach a maximum swing range in the width direction when the rotation handle is rotated 10 to 20 revolutions.

According to the invention of claim 10, the center of the swing motion of the swing unit may be at the central position in the width direction and may be located above in a horizontal direction than an upper surface of any one of the head support, the waist support, and the body support.

According to the invention of claim 11, there is provided a patient body measurement method using the treatment table according to any one of claims 1 to 10, the method including using a body measurement level gauge including using holders which are flat plates erected in a state of being in contact with both left and right sides of the body of a patient in a state of lying on the belly, a horizontal rod provided on upper edges of the holders and placed on an upper surface of the body of the patient, and a level attached to the horizontal rod, and adjusting the swing unit so that the level is horizontal to measure a swing position at that time.

According to the invention of claim 12, there is provided a patient body measurement method using the treatment table which improves body balance, according to any one of claims 1 to 10, the method including using a body measurement level gauge including using holders which are flat plates erected in a state of being in contact with both left and right sides of the body of a patient in a state of lying on the belly, a horizontal rod provided on upper edges of the holders and placed on an upper surface of the body of the patient, and a level attached to the horizontal rod, adjusting the swing unit so that the level is horizontal to measure a swing position at that time, holding the patient's body at the swing position, and adjusting the swing unit again so that the level is horizontal after a predetermined period is elapsed to measure the swing position at that time.

Effects of the Invention

According to the present invention, since the head support and the waist support can swing in the width direction about the central position in the width direction and the adjustment operation units for adjusting the swing units are disposed at one concentrated position of the treatment table, the supports can be directly adjusted by one operator while checking the body state of the patient. Moreover, the body support can be swung.

Due to this, it is possible to improve the treatment effects and to reduce the operator's labor.

Since the treatment table includes the link mechanism for connecting the swing unit and the adjustment operation unit, it is possible to provide a treatment table of which the maintenance is easy and which does not require a power supply.

According to a configuration in which the treatment table includes the driving units for driving the swing units of the above head support, the body support, and the waist support and uses the switches for electrically controlling the driving units, a treatment table with which it is easy to focus on adjustments of directions without using force can be realized.

In the configuration in which the treatment table includes the sensor unit for detecting a swing position of the swing unit, the storage unit for storing a detection value obtained by the sensor unit, and the output unit for outputting the stored detection value, by recording the patient's present and past detection values, it is possible to compare the body's distortion during treatments, check the treatment effects, and draw up a treatment plan.

In particular, in the configuration in which the treatment table includes the driving unit, it is easy to install the driving unit together with the sensor unit and the treatment table can be easily realized at a low cost.

In the configuration in which the treatment table further includes the chest support for supporting the chest of the patient, when the length in the longitudinal direction of the body support is shorter than the length of the chest support, it is possible to provide a treatment table adapted to short patients.

That is, the conventional treatment table was configured such that the length of the body support is longer than the length of the chest support so as to be adapted to patients having a large physique. However, according to the study of the present inventors, it has been found that it is optimal to shorten the length of the body support when the treatment table is shortened. With the present invention, it is possible to reliably hold patients of various physiques.

In the above length setting, it is preferable to dispose the body support at a position that the anterior superior iliac spine of the patient, in particular, is held by the body support. By doing so, it is possible to shorten the length in the longitudinal direction of the body support.

According to the patient body measurement method using the treatment table, since it is possible to measure the distortion of a patient's body easily and with high accuracy, it is possible to easily adjust the treatment table during treatments and to accurately understand the treatment effects by comparing the present adjustment position with the previous adjustment position.

MODE FOR CARRYING OUT THE INVENTION

A treatment table according to an embodiment of the present invention will be described with reference to FIGS. 1 to 9. The present invention can be arbitrarily changed within the range disclosed in the claims.

The treatment table 1 is used mainly for treatments of vertebral joints such as a cervical spine and is an operation table with which an operator performs treatments or surgical operations for vertebral joints of a patient in a state in which the patient lies on the table and the head and the waist are supported.

Figure 1:
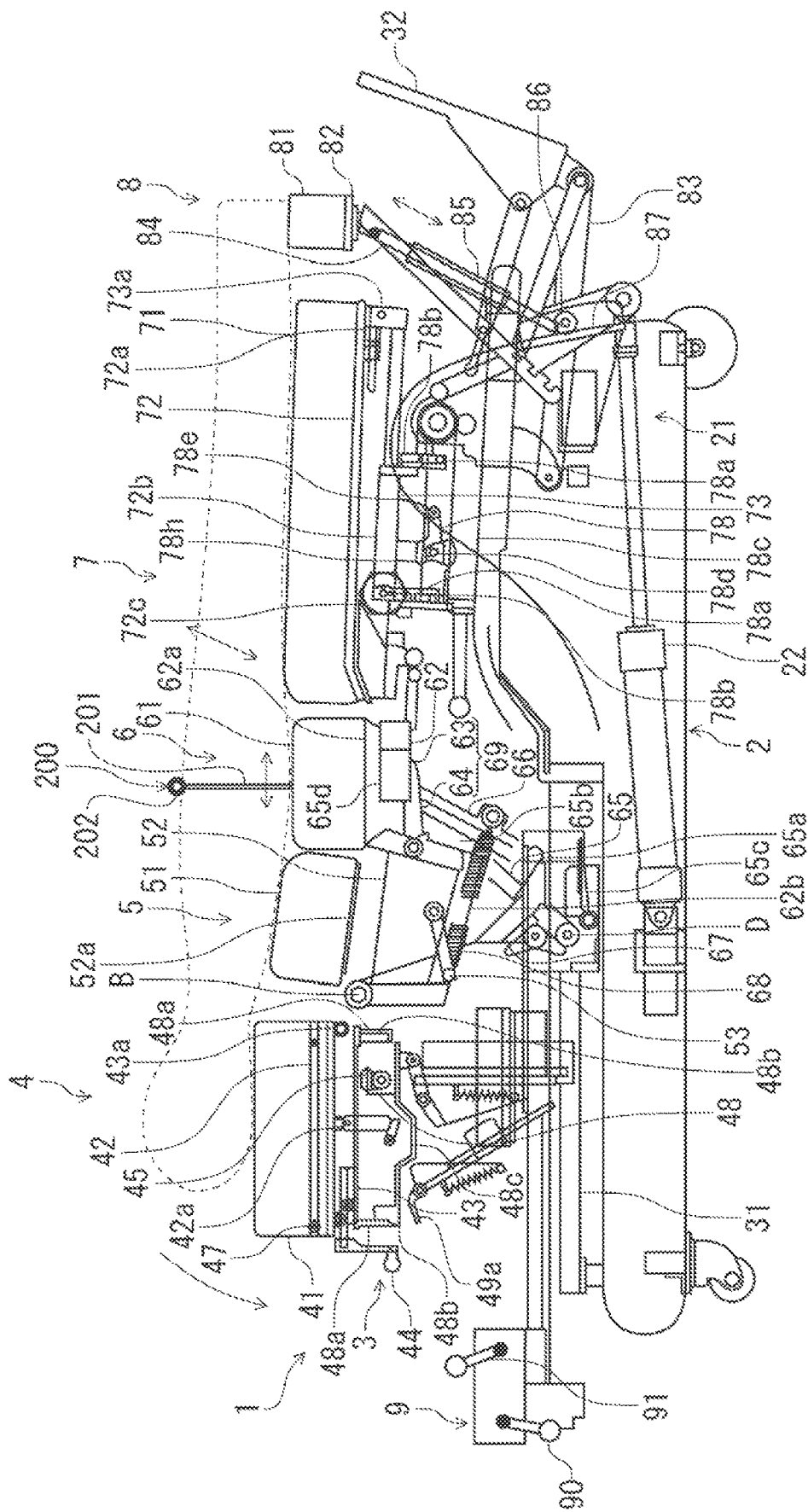
FIG. 1 is a front view illustrating an outline of a treatment table according to an embodiment of the present invention.
Figure 2:
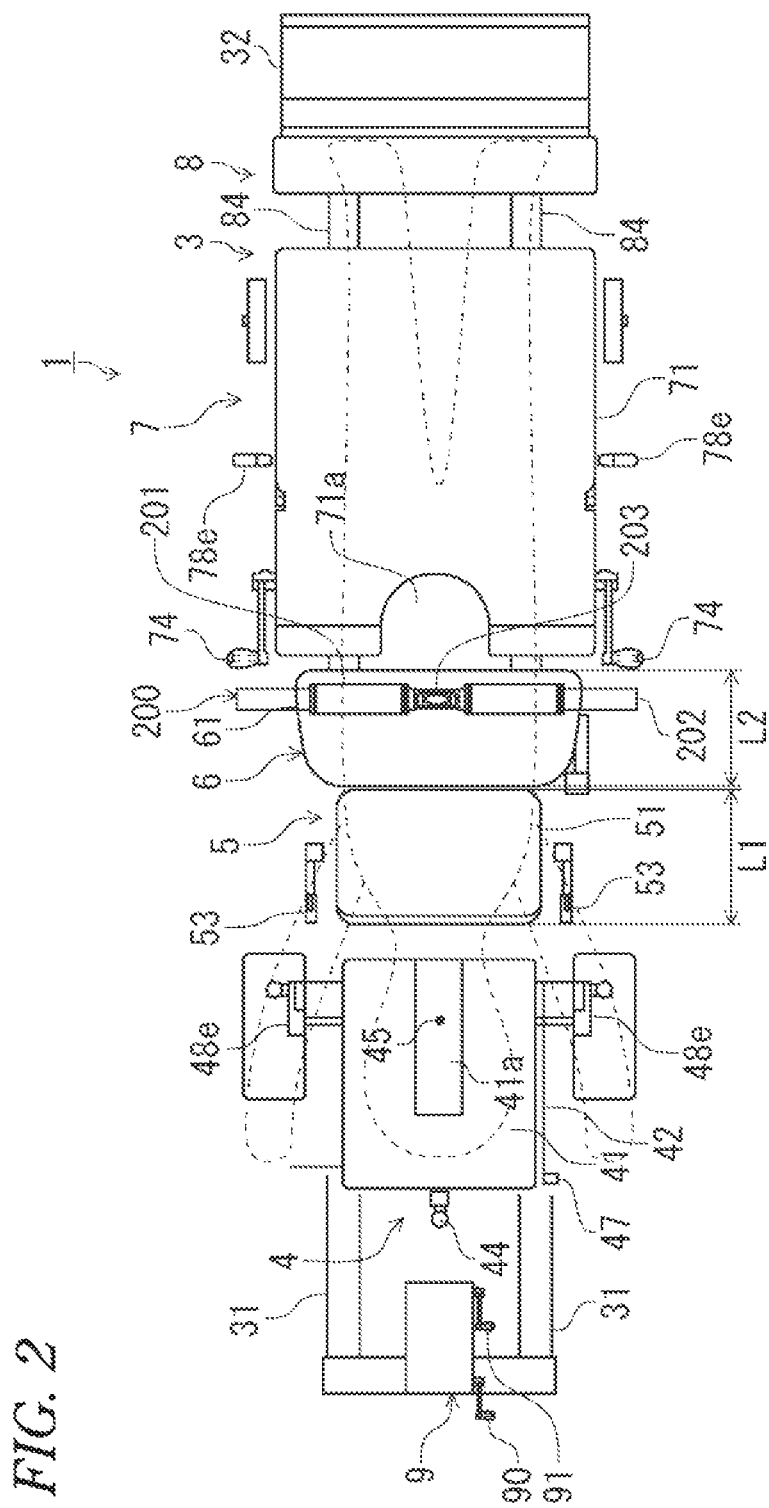
FIG. 2 is a plan view illustrating an outline of the above treatment table.

Specifically, as illustrated in FIGS. 1 and 2, the treatment table 1 has a bed-shaped treatment table body 3 provided on a machine table 2 configured to be able to travel.

The treatment table body 3 includes a head support 4 for supporting the head of a patient when the patient lies on the treatment table body 3, a chest support 5 for supporting the chest of the patient, a body support 6 for supporting the body of the patient, a waist support 7 for supporting the waist of the patient, and a leg support 8 for supporting the legs of the patient. The head support 4, the chest support 5, the body support 6, the waist support 7, and the leg support 8 are arranged in a longitudinal direction of the treatment table body 3.

Further, the treatment table body 3 is configured to be able to rotate and move up and down about a base end of the treatment table body 3 with the aid of a lift mechanism 21 attached to the machine table 2. The lift mechanism 21 includes a hydraulic cylinder 22 as a driving unit having one end connected to a position located close to a distal end, which is located closer to the head support 4 than the central position in the longitudinal direction of the machine table 2.

On the other hand, the treatment table body 3 includes a pair of body frames 31, and the base ends of the pair of body frames 31, located closer to the leg support 8 are rotatably connected to the machine table 2. The other end of the hydraulic cylinder 22 is rotatably connected between the machine table 2 and the base ends of the pair of frames 31.

The distal end of the treatment table body 3 can be moved upward by the driving of the hydraulic cylinder 22 so that the treatment table body 3 can stand up by approximately 63°, for example, from a horizontal position.

Further, a footstool 32 on which the feet of the patient is placed so that the patient can stand up when the treatment table body 3 is rotated so as to stand up is attached to the base ends of the pair of frames 31.

The footstool 32 is configured to rotate about the base end of the footstool 32 in synchronization with the standing up and the operation of the treatment table body 3 by the hydraulic cylinder 22 of the lift mechanism 21.

Figure 5:
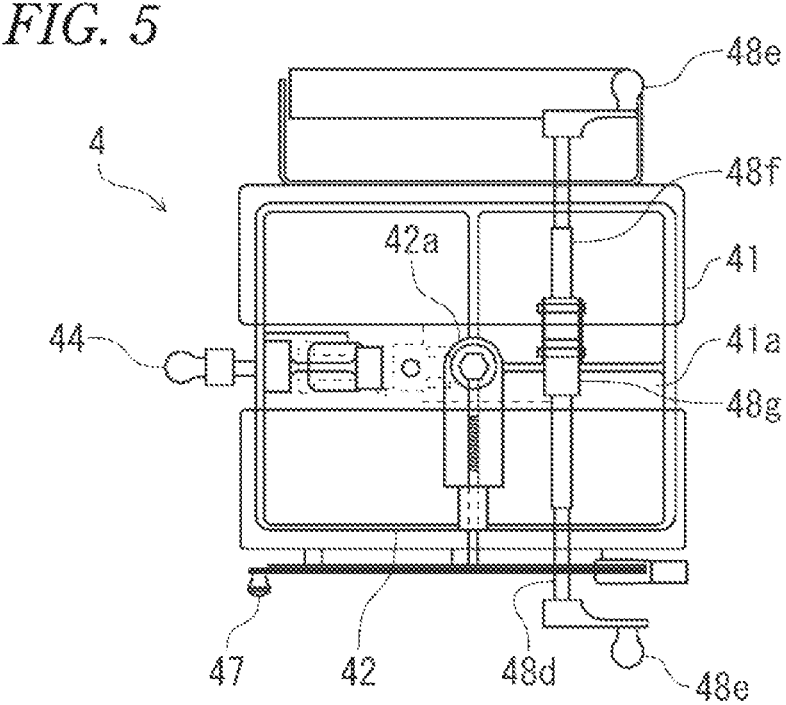
FIG. 5 is a plan view illustrating an outline of a head support of the above treatment table.
Figure 6:
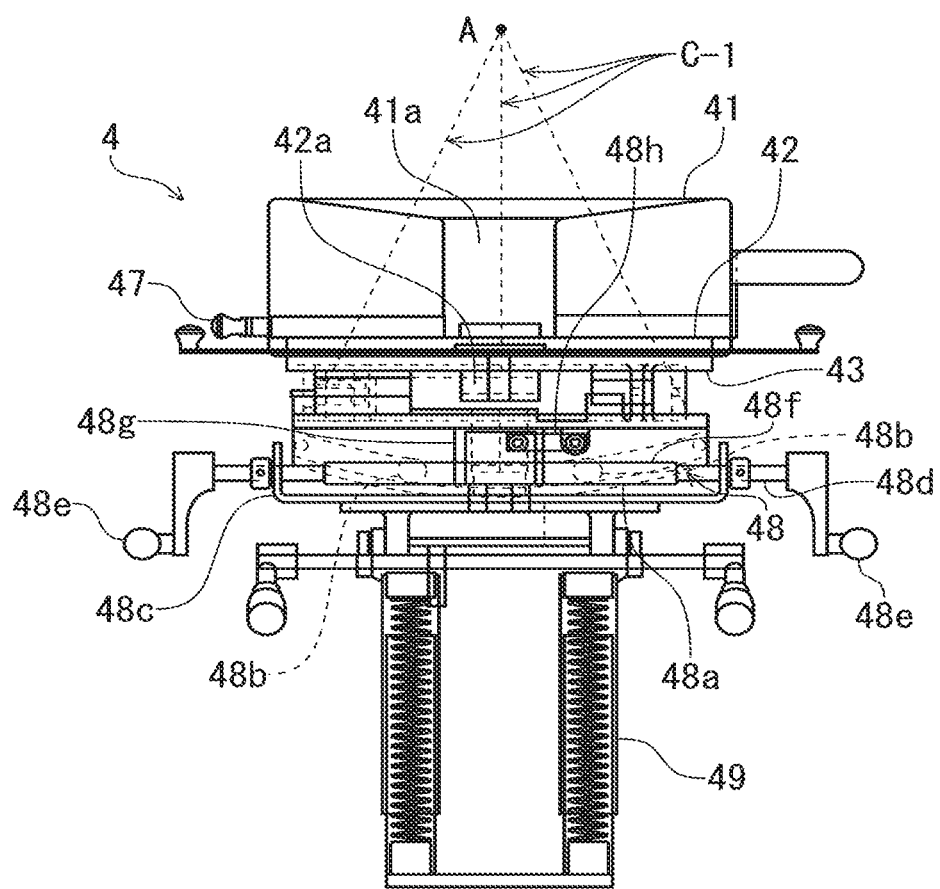
FIG. 6 is a left side view illustrating an outline of the head support of the above treatment table.

A plan view illustrating an outline of the head support 4 is illustrated in FIG. 5, and the left side view thereof is illustrated in FIG. 6. The head support 4 is attached to the distal ends of the pair of body frames 31 and includes a head mat 41 having an approximately concave shape in a plan view. The head mat 41 is placed on and attached to a flat head plate 42 in a state in which an end close to a concave opening 41a faces a base end of the head plate 42. The base end of the head plate 42 is attached so as to be rotatable in an up-down direction by a connecting portion 43a provided on a base end side of a flat head swing plate 43.

The head plate 42 is configured such that, when a lifting handle 44 attached to the central position close to the distal end of the head plate 42 is rotated, the distal end of the head plate 42 is rotated in the up-down direction about the connecting portion 43a close to the base end of the head plate 42 so that the distal end of the head plate 42 can be tilted by being moved up by approximately 7 mm, for example, from the horizontal position.

Further, the central position close to the base end of the head swing plate 43 is rotatably connected to a rotation shaft 45 (FIG. 2) of which the axial direction extends in the up-down direction, and the head swing plate 43 is attached so as to be able to rotate in the horizontal direction about the rotation shaft 45.

Here, as illustrated in FIG. 2, the head swing plate 43 is configured so as to be able to rotate in a horizontal direction by 15° in each width direction about the rotation shaft 45 from a state in which the longitudinal direction of the head swing plate 43 extends in the longitudinal direction of the machine table 2. Moreover, the head swing plate 43 is configured such that the head mat 41 can be rotated to a predetermined angle by an operator holding and moving swing bars 47 attached to both ends in the width direction of the head plate 42.

As illustrated in FIG. 6, a head swing mechanism 48 is provided below the head swing plate 43 so as to allow the head mat 41 of the head support 4 to swing in the width direction about a support point A located above the central position in the width direction of the head mat 41. The head swing mechanism 48 includes a pair of rails 48a having an L-shaped cross-section bent in a concave arc shape and is attached to both ends in the longitudinal direction of a lower surface of the head swing plate 43 in a state in which these rails 48a face each other. Here, these rails 48a are formed to be bent in such a curvature that the support point A is at the central position.

A pair of cam followers 48b which are columnar rollers is rotatably stored in these rails 48a, and the cam followers 48b are locked so as to be movable in the bending direction of these rails 48a in relation to each other.

Here, these cam followers 48b are rotatably attached to both ends in the longitudinal direction of a connection base 48c, and an interlocking shaft 48d is attached along the width direction of the connection base 48c.

The interlocking shaft 48*d* moves a cylindrical member 49*g* fitted to a trapezoidal screw 48*f* in an axial direction when an operator rotates rotation handles 48*e* attached to both ends of the interlocking shaft 48*d* to rotate the trapezoidal screw 48*f* attached to an intermediate portion of the interlocking shaft 48*d*. The other end of a link plate 48*h* having one end rotatably connected to the cylindrical member 48*g* and the other end rotatably connected to the head swing plate 43 is moved in the axial direction of the interlocking shaft 48*d* so that the head swing plate 43 swings (that is, turns (twists)) by 10°, for example, from the central position along the bending direction of the pair of rails 48*a*.

Further, a head lift mechanism 49 is attached to a lower side of the head swing mechanism 48 and the head mat 41 of the head support 4 is moved in the up-down direction by approximately 90 mm, for example, when an operator operates a pedal 49*a* of the head lift mechanism 49.

Here, a motor for driving the interlocking shaft 48*d* may be provided so that the above head swing mechanism 48 is electrically driven by electrically controlling the motor (not illustrated).

An existing gear mechanism may be disposed between the motor and the interlocking shaft 48*d* so that an operator can operate the rotation handle 48*e* and perform motor-based driving.

When electric control is performed, an operation switch for performing an adjustment operation can be provided in an arbitrary place of the treatment table.

Moreover, an operator may perform an adjustment operation at another place with the aid of a link mechanism which uses gears, transmission rods, and the like and is connected to the interlocking shaft 48*d*. For example, when a level for checking the horizontality of the treatment table is provided so that an operator can perform operations near the level, the operator can easily perform accurate leveling.

Moreover, when the operator is allowed to perform operations near a position (for example, the position on the central line of the body such as above the head or below the legs) where it is easy to check the distortion or the like of the patient's body, it is possible to perform a highly accurate surgical operation.

A configuration in which the head swing mechanism 48 is controlled by the above motor-based driving and a configuration in which an adjustment operation can be performed at another place with the aid of the link mechanism will be described in detail later.

A head drop mechanism 42*a* which is moved up by a predetermined interval (for example, approximately 7 mm) and is locked when the head mat 41 is pulled upward and with which the head mat 41 is slid by a predetermined interval (for example, approximately 7 mm) when predetermined pressure is applied from above to the head mat 41 is provided between the head swing plate 43 and the head plate 42 of the head support 4.

Figure 7:
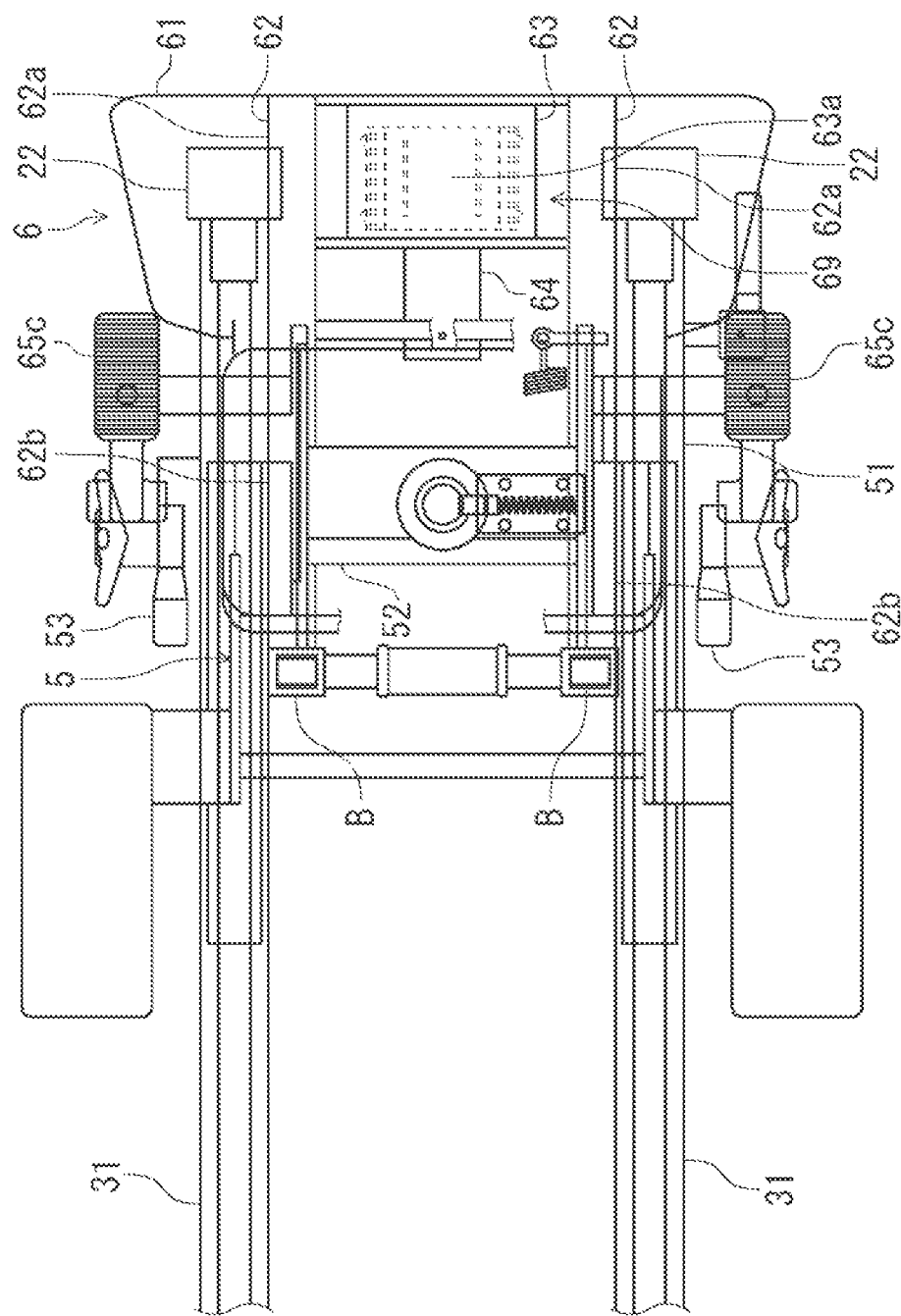
FIG. 7 is a plan view illustrating an outline of a chest support and a body support of the above treatment table.

Next, the chest support 5 will be described. A plan view illustrating an outline of the chest support 5 and the body support 6 is illustrated in FIG. 7. In implementation of the present invention, the arrangement of the chest support 5 is not necessarily essential but the chest support 5 may be integrated with the body support 6, for example.

The chest support 5 includes a chest mat 51 having an approximately rectangular shape in a plan view, and the chest mat 51 is attached to a flat attachment plate 52 so as to be movable up and down.

As illustrated in FIG. 1, the attachment plate 52 is attached so that the front-rear direction of the attachment plate 52 is inclined downward toward the body support 5 in a state in which the front-rear direction of the body support 6 is positioned horizontally.

Thus, the chest mat 51 is configured to be movable up and down along the inclination direction inclined downward by approximately 40° to 50°, for example, toward the head support 4.

Moreover, as illustrated in FIG. 1, the attachment plate 52 is connected so that the distal end thereof can rotate about a first support point B located between the head support 4 and the chest support 5. Specifically, the attachment plate 52 is configured so that the distal end of the chest mat 51 is moved up to be inclined by approximately 11 mm, for example, from the horizontal position. Moreover, an operating lever 53 for operating rotation about the first support point B of the chest mat 51 is attached to a lower portion of the attachment plate 52.

A chest drop mechanism 52*a* which is moved up by a predetermined interval (for example, approximately 11 mm) and is locked when the chest mat 51 is pulled upward and with which the chest mat 51 is slid downward by a predetermined interval (for example, approximately 11 mm) when predetermined pressure is applied from above to the chest mat 51 is provided between the chest mat 51 of the chest support and the attachment plate 52.

Next, the body support 6 includes a body mat 61 having an approximately rectangular shape in a plan view, and the body mat 61 is provided on flat portions 62*a* of a pair of body mat frames 62.

A swing box 63 as a rotation adjustment unit is attached to a lower portion of the body mat 61, and the swing box 63 is inserted and attached between the flat portions 62*a* of the body mat frames 62. A groove 63*a* formed along the front-rear direction of the body support 6 is provided inside the swing box 63.

Moreover, a stopper 64 as a locking unit is attached to a position close to distal ends of bent portions 62*b* bent in an approximately C-shape, located close to the base ends of the body mat frames 62, and the distal end of the stopper 64 can be inserted into the swing box 63.

The base end of the bent portion 62*b* of the body mat frame 62 is attached so as to be rotatable about the first support point B, and the body mat 61 is attached so as to be movable about the first support point B together with the chest mat 51 of the chest support 5 that is rotatably attached to the first support point B.

The chest mat 51 and the body mat 61 are configured so as to be rotatable by approximately 14° toward the lower side from an approximately horizontal position (for example, a position raised by approximately 3° from the horizontal position) about the first support point B. Further, a gas cylinder 65 as a holding unit capable of adjusting and holding the rotation position of the chest mat 51 and the body mat 61 is attached between the machine table 2 and a position close to the base ends of the flat portions 62*a* of the body mat frames 62.

As illustrated in FIG. 1, the gas cylinder 65 is attached to be inclined downward toward the distal end from the base end of the machine table 2. The distal end of the piston portion 65*a* of the gas cylinder 65 is rotatably connected to the machine table 2 under the chest mat 61. The distal end of the piston portion 65*a* serves as a second support point D different from the first support point B.

Moreover, the gas cylinder 65 is configured so that, when a pedal 65*c* provided on a machine body near a position to which the distal end of the piston portion 65*a* of the gas cylinder 65 is connected is operated, the piston portion 65*a* of the gas cylinder 65 advances and retracts, and the rotation angle of the chest mat 51 and the chest mat 61 about the first support point B can be controlled by controlling the stroke (length) of the gas cylinder 65.

Further, an engagement portion 65d having a circular shape in a side view is formed in the base end of a cylinder portion 65b of the gas cylinder 65, and the engagement portion 65d is slidably and rotatably stored in the groove 63a of the swing box 63.

The gas cylinder 65 is attached so as to be able to move (that is, swing) in the longitudinal direction of the groove 63a (that is, on the straight line along the flat portion 62a).

Further, the engagement portion 65d is configured to engage with the distal end of the stopper 64 at a position at which the engagement portion 65d can move to the frontmost side in the groove 63a of the swing box 63. The rotation of the body mat 61 in the up-down direction about the first support point B, resulting from the engagement portion 65d sliding inside the groove 63a of the swing box 63 is locked other than the rotation of the body mat 61 in the up-down direction about the first support point B resulting from the gas cylinder 65 advancing and retracting when the engagement portion 65d is engaged by the stopper 64.

Thus, the engagement portion 65d and the stopper 64 form an engagement holding mechanism 69 as a lock mechanism that locks the rotation of the body mat 61 about the first support point B when the engagement portion 65d slides within the groove 63a of the swing box 63.

Moreover, one end of a link frame 66 is rotatably connected to the engagement portion 65d of the cylinder portion 65b of the gas cylinder 65. The other end of the link frame 66 is rotatably connected to a position located closer to the base end of the machine table 2 than the connection position of the distal end of the piston portion 65a of the gas cylinder 65.

Moreover, one end of the support frame 67 is rotatably connected to the other end of the link frame 66, and the other end of the support frame 67 is rotatably connected to the legs close to the base ends of the bent portions 62b of the body mat frames 62.

Further, a spring 68 as a rotation adjustment unit is attached between an intermediate portion of the link frame 66 and the legs close to the base ends of the bent portions 62b of the body mat frames 62 to which the other end of the support frame 67 is connected.

The spring 68 is configured to apply predetermined tension between the body mat 61 and the first support point B (specifically between the intermediate portion of the link frame 66 and the bent portion 62b of the body mat frame 62). By the elastic force of the spring 68, the rotation position of the chest mat 51 and the body mat 61 about the first support point B is maintained to some extent in a state in which the stopper 64 is disengaged from the engagement portion 65d in the groove 63a of the swing box 63 so that the rotation of the chest mat 51 and the body mat 61 about the first support point B can be adjusted more reliably.

That is, the swing box 63 is configured so that the rotation of the chest mat 51 and the body mat 61 about the first support point B is adjusted by the operation of the gas cylinder 65, and when the stopper 64 is disengaged from the engagement portion 65d stored so as to be able to slide in the groove 63a of the swing box 63 from the aligned position, the engagement portion 65d close to the rotatably connected base ends of the gas cylinder 65 and the link frame 66 can swing inside the groove 63a of the swing box 63, and the rotation of the chest mat 51 and the body mat 61 about the first support point B can be adjusted using the operating lever 53.

Therefore, the chest mat 51 and the body mat 61 can be rotated about the first support point B according to the advancing and retracting operations of the gas cylinder 65 using the pedal 65c. Moreover, the chest mat 51 and the body mat 61 can be rotated using the operating lever 53 about the first support point B while the rotation of the body mat 61 is maintained to some degree by the elastic force of the spring 68 when the stopper 64 is rotated to be disengaged from the engagement portion 65d in the groove 63a of the swing box 63. Thus, the chest mat 51 and the body mat 61 can be adjusted in two steps by the adjustment of the gas cylinder 65 and the operating lever 53.

As another embodiment, in place of or in addition to the above gas cylinder 65, an existing actuator may be provided so that driving based on electric control can be performed.

In this case, by introduction of electric control, a switch as an adjustment operation unit can be disposed in an arbitrary place of the treatment table.

In the treatment table 1 in which the head support 4, the chest support 5, the body support 6, and the waist support 7 are arranged in the longitudinal direction as in the present embodiment, there was a case in which the body of a short patient was not necessarily satisfactorily held on a conventional treatment table. Thus, the present inventors have studied the balance between the lengths of the respective supports 4, 5, 6, and 7 and invented the treatment table 1 capable of holding patients of various physiques optimally.

As a result, the present inventors have found that it is important in surgical operations to hold the anterior superior iliac spine of a patient's pelvis separately from the chest and the waist and shortened the length of the body support 6 as compared to the conventional table. Moreover, the present inventors have found that surgical operations on the whole body of a short patient can be performed satisfactorily when the shortened body support 6 reliably holds the anterior superior iliac spine.

In this respect, conventionally, the ratio of the chest support and the body support was set according to the ratio of the lengths of respective parts of an ordinary body so that the body support is longer than the chest support. Thus, the respective parts are generally shortened by the same ratio to shorten the entire length. However, in this case, the positions of the respective supports do not fit a tall patient and it is difficult to perform surgical operations. According to the present invention, the unshortened chest support and the waist support can hold the respective parts of a patient properly by aligning the anterior superior iliac spine with the body support.

The length L2 of the body support is preferably shorter than the length L1 of the chest support in order to realize the above mentioned configuration. That is, the length of the conventional treatment table 1 is set such that the head support is 330 mm, the chest support is 200 mm, the body support is 300 mm, the waist support is 620 mm, and the leg support is 100 mm. However, according to the treatment table of the present invention, the body support is shortened to 150 mm and the lengths of the other supports are maintained.

Figure 8:
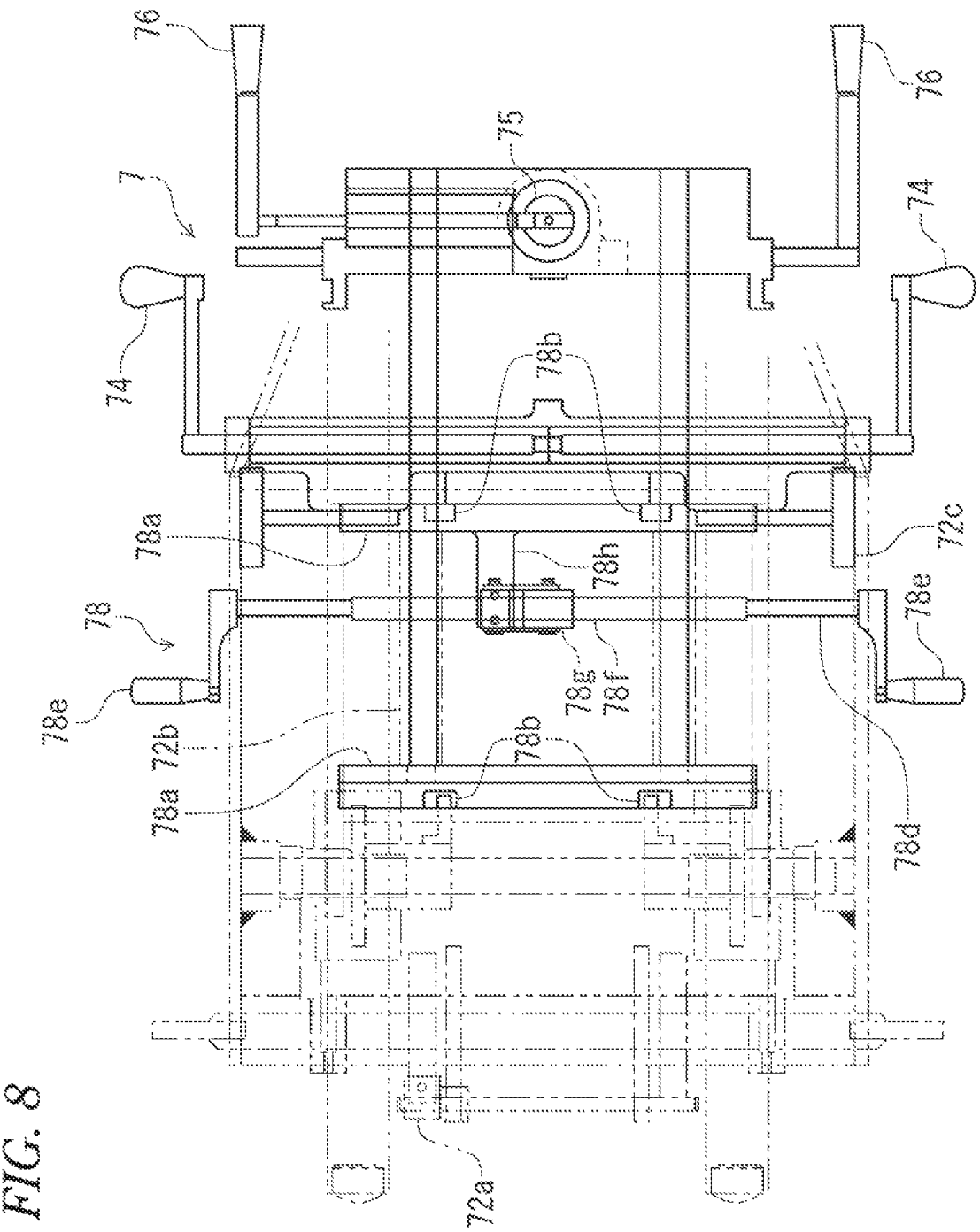
FIG. 8 is a plan view illustrating an outline of a waist support of the above treatment table.
Figure 9:
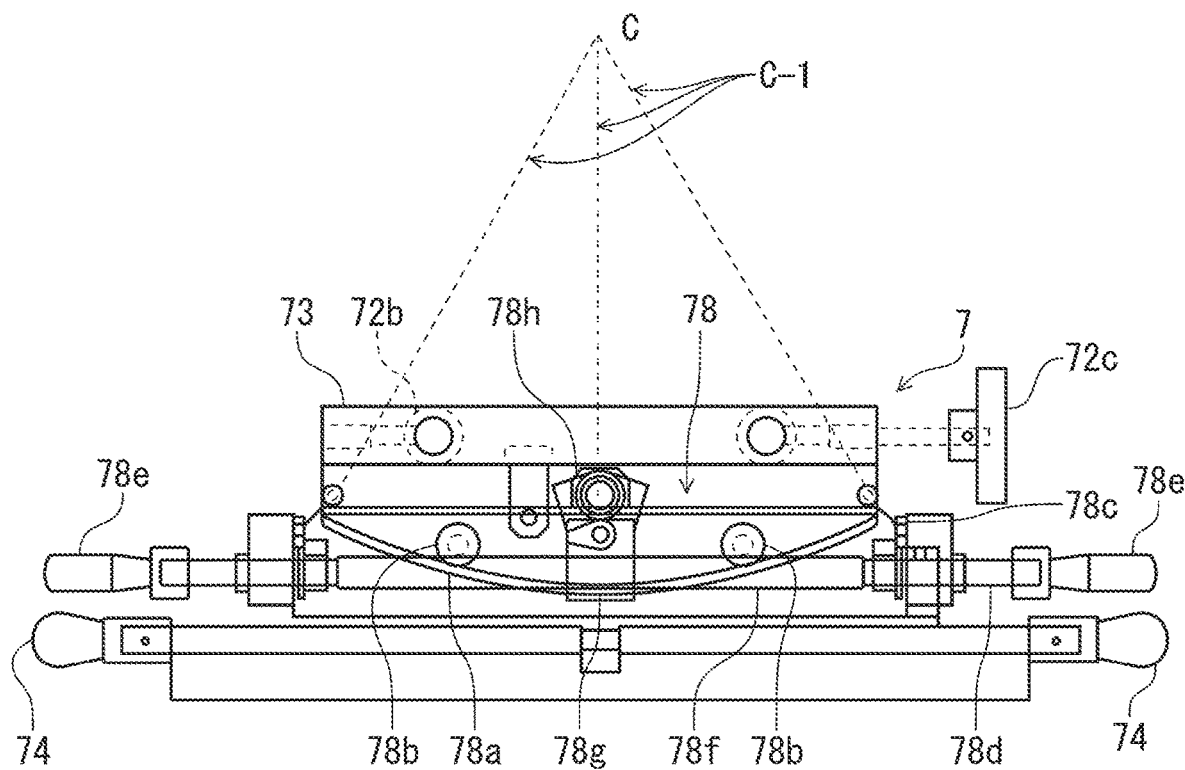
FIG. 9 is a left side view illustrating an outline of the waist support of the above treatment table.

Next, the waist support 7 will be described. FIG. 8 is a plan view illustrating an outline of the waist support 7 and FIG. 9 is a left side view.

The waist support 7 is attached to the base ends of the pair of body frames 31 and includes a waist mat 71 having an approximately concave shape in a plan view.

The waist mat 71 is provided on and attached to a flat waist plate 72 in a state in which a concave opening 71*a* faces the distal end (see FIGS. 1 and 2).

The base end of the body plate 72 is connected so as to be rotatable in the up-down direction by a connecting portion 73*a* provided on the base end side of a flat waist swing plate 73.

The waist plate 72 is configured such that, when an operator grasps and moves up and down knobs 74 attached to both side portions close to the distal end of the waist plate 72, the distal end of the waist plate 72 can be rotated upward by approximately 20°, for example, and moved up from the horizontal position about the connecting portion 73*a* close to the base end of the waist plate 72.

Moreover, as illustrated in FIG. 8, the central position in the width direction close to the distal end of the waist swing plate 73 is rotatably connected to a rotation shaft 75 having an axial direction extending in the up-down direction, and the waist swing plate 73 is attached so as to be rotatable in the horizontal direction about the rotation shaft 75. Here, the waist swing plate 73 is configured to be rotatable horizontally toward each width direction from a state in which the longitudinal direction of the waist swing plate 73 extends in the longitudinal direction of the machine table 2, and the waist mat 71 can be rotated horizontally by a predetermined angle when an operator grasps and moves swing bars 76 attached to both side portions close to the base end of the waist plate 72.

As illustrated in FIG. 9, a waist swing mechanism 78 is provided below the waist swing plate 73 so as to allow the waist mat 71 of the waist support 7 to swing in the width direction about a support point C located above the central position in the width direction of the waist mat 71.

The waist swing mechanism 78 includes a pair of rails 78*a* having an L-shaped cross-section bent in a concave arc shape and is attached to both ends in the longitudinal direction of the lower surface of the waist swing plate 73 in a state in which these rails 78*a* face each other.

These rails 78*a* are formed to be bent in such a curvature that the support point C is at the central position. A pair of cam followers 78*b* which are cylindrical rollers is rotatably stored in the rails 78*a*, and the cam followers 78*b* are locked so as to be movable in the bending direction of these rails 78*a* in relation to each other.

The cam followers 78*b* are rotatably attached to both ends in the longitudinal direction of a connection base 78*c*, and an interlocking shaft 78*d* is attached along the width direction of the connection base 78*c*. As illustrated in FIGS. 8 and 9, the interlocking shaft 78*d* moves a cylindrical member 78*g* fitted to a trapezoidal screw 78*f* in the axial direction when an operator rotates rotation handles 78*e* attached to both ends of the interlocking shaft 78*d* to rotate the trapezoidal screw 78*f* attached to an intermediate portion of the interlocking shaft 78*d*. The other end of a link plate 78*h* having one end rotatably connected to the cylindrical member 78*g* and the other end rotatably connected to the waist swing plate 73 is moved in the axial direction of the interlocking shaft 78*d* so that the waist swing plate 73 swings by 10°, for example, from the central position along the bending direction of the pair of rails 78*a*.

Here, a motor for driving the interlocking shaft 78*d* may be provided so that the above waist swing mechanism 78 is electrically driven by electrically controlling the motor (not illustrated).

An existing gear mechanism may be disposed between the motor and the interlocking shaft 78*d* so that an operator can operate the rotation handle 78*e* and perform motor-based driving.

When electric control is performed, an operation switch for performing an adjustment operation can be provided in an arbitrary place of the treatment table.

Moreover, an operator may perform an adjustment operation at another place with the aid of a link mechanism which uses gears, transmission rods, and the like and is connected to the interlocking shaft 78*d*. For example, when a level for checking the horizontality of the treatment table is provided so that an operator can perform operations near the level, the operator can easily perform accurate leveling. Moreover, during surgical operations, it is preferable that the external occipital protuberance of the occipital region and the intergluteal cleft of the gluteal region are horizontal so that an adjustment operation can be performed while checking the horizontality of these regions.

In this manner, when the operator is allowed to perform operations near a position (for example, the position on the central line of the body such as above the head or below the legs) where it is easy to check the distortion or the like of the patient's body, it is possible to perform highly accurate surgical operations.

A waist drop mechanism 72*a* which is moved up by a predetermined interval (for example, approximately 11 mm) and is locked when the waist mat 71 is pulled upward and with which the waist mat 71 is slid downward by a predetermined interval (for example, approximately 11 mm) when predetermined pressure is applied from above the waist mat 71 is provided between the waist plate 72 and the waist swing plate 73.

A slide mechanism 72*b* is provided between the waist plate 72 and the waist swing plate 73 so as to allow the waist plate 72 to be slidable in the longitudinal direction (that is, the front-rear direction) in relation to the waist swing plate 73. The slide mechanism 72*b* allows the waist plate 72 to slide in the longitudinal direction when an operator operates a handle 72*c* attached to the waist swing plate 73 to unlock the locking between the waist swing plate 73 and the waist plate 72 and the sliding position of the waist plate 72 is locked when the operator operates the handle 72*c* to lock the waist swing plate 73 and the waist plate 72.

As described above, in the treatment table 1 according to the present invention, swing mechanisms for the head support 4 and the waist support 7 are provided so that an inclination in the left-right direction of a patient can be adjusted by a rotation handle.

As illustrated in FIG. 2, in the conventional configuration, the inclination of the head support 4 is adjusted by the rotation handle 48*e* provided on a side portion of the head support 4, and the head support 7 is adjusted by the rotation handle 48*e* provided on a side portion of the waist support 7.

When the rotation handles are disposed in such a distributed manner, an operator needs to perform adjustments while moving around the treatment table 1 and it is difficult to perform adjustments while checking the direction of the patient's body from an optimal position. Thus, conventionally, it was necessary to perform adjustments with the aid of an assistant.

The present invention solves such a conventional problem according to the following two methods.

That is, a first method involves performing operations by connecting the interlocking shafts 48*d* and 78*d* to an adjustment operation unit at one position of the treatment table using link mechanisms and a second method involves arranging motors for driving the interlocking shafts 48d and 78d, arranging switches which are adjustment operation unit of the motors at one concentrated position of the treatment table, and performing operations.

According to the first method, as illustrated in FIGS. 1 and 2, for example, the adjustment operation unit 9 is arranged on a further front side of the head support 4 and the link mechanisms are connected from the interlocking shafts 48d and 78d.

The adjustment operation unit 9 includes two rotation handles 90 and 91, and the front rotation handle 90 is linked to a rotation operation of the interlocking shaft 48d of the head support 4, and the rear rotation handle 91 is linked to a rotation operation of the interlocking shaft 78d of the waist support 7.

Since an operator can operate the rotation handles 90 and 91 while viewing the trunk from above the head of a patient, it is possible to perform an optimal adjustment operation without requiring an assistant.

The adjustment operation unit 9 may be disposed below the leg support 8 without being limited to the illustrated position.

Figure 3:
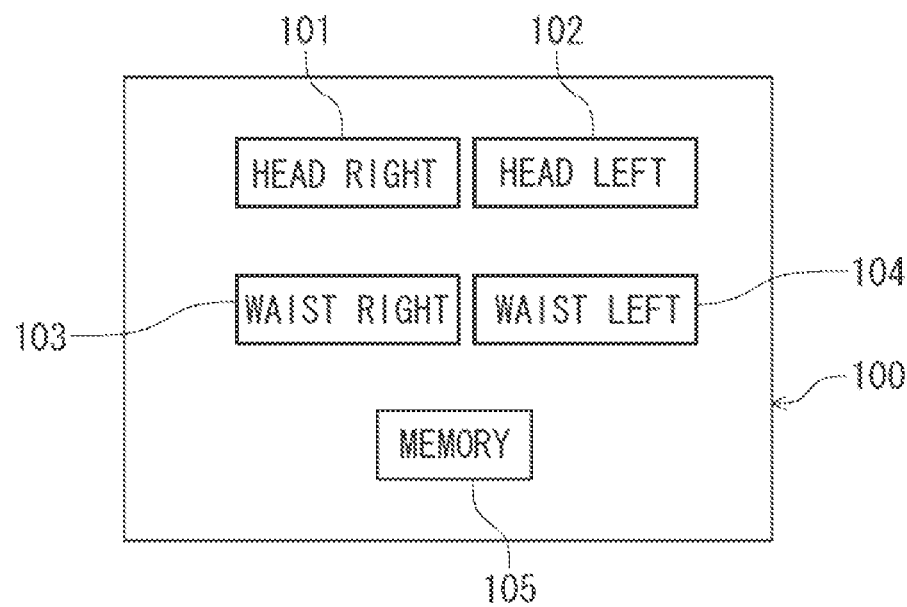
FIG. 3 is a schematic diagram illustrating an outline of an operation panel according to the present invention.

The second method will be described with reference to FIG. 3. FIG. 3 is a schematic diagram illustrating an outline of an operation panel 100 according to the present invention.

The operation panel 100 includes a plurality of switches as illustrated in the drawing, which includes a head right switch 101 for inclining the head support 4 to the right side, a head left switch 102 for inclining the head support 4 to the left side, a waist right switch 103 for inclining the waist support 7 to the right side, and a waist left switch 104 for inclining the waist support 7 to the left side. Further, a memory switch 105 described later is also provided.

For example, when an operator presses on the head right switch 101, a motor for driving the interlocking shaft 48d is rotated in a predetermined direction and the head support 4 is inclined to the right side. Similarly, when an operator presses on the head left switch 102, the motor is rotated in a reverse direction and the housing 4 is inclined to the left side. The same operation is performed on the waist support 7.

When the adjustment operation is motorized so that operations can be performed at one concentrated position, the operator can adjust the directions of the patient's body very conveniently. Moreover, since adjustments can be performed while viewing from an optimal direction, the surgical operation accuracy can be improved.

Figure 4:
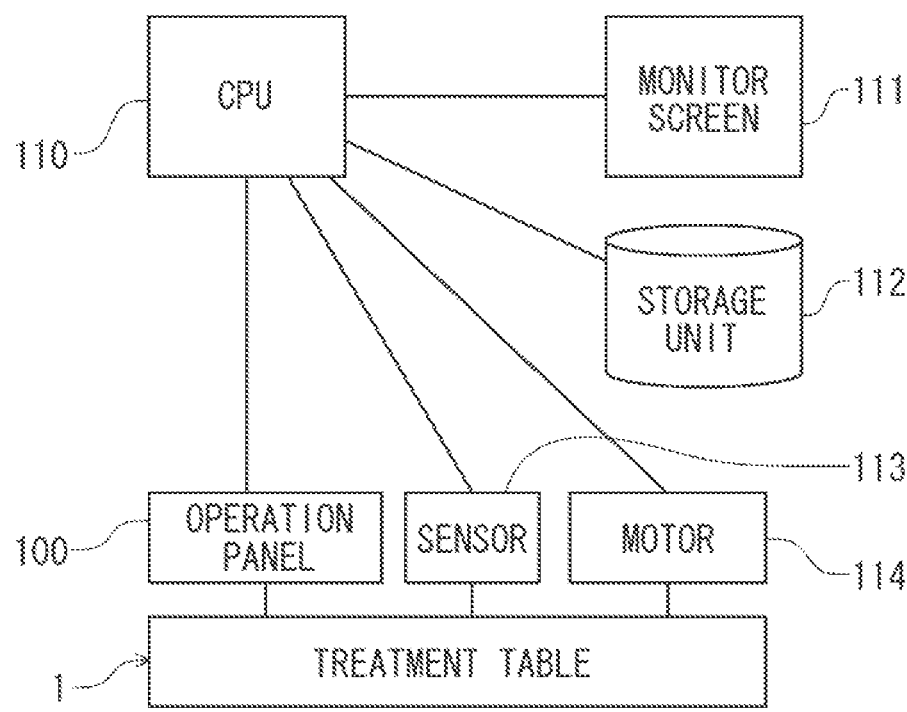
FIG. 4 is a diagram of a system for motorizing an adjustment operation.

The present invention may include a computer system for storing the distortion or the like of a patient. FIG. 4 is a diagram of a system for motorizing the adjustment operation.

The computer system includes a CPU 110 realized by an existing computer, a monitor screen 111 that displays a processing content on a screen, and a storage unit 112 such as a hard disc, the CPU 110 is connected to the operation panel 100, a sensor 113, and a motor 114 attached to the treatment table 1.

In this configuration, the sensor 113 detects the swing positions of the head swing mechanism 48 and the waist swing mechanism 78 of the treatment table 1. An existing position detection sensor may be appropriately used as the sensor 113.

The detection value obtained by the sensor 113 is input to the CPU 110 and is stored in the storage unit 112 together with identification data of a patient, which is input separately.

The operator can call the data obtained in the previous surgical operation, for example, and use the same in the present surgical operation while checking a change or the like in the distortion of the body by checking the monitor screen 111.

Moreover, when the operator operates the above switches of the operation panel 100 while checking the present detection value obtained by the sensor 113 on a realtime basis, it is possible to perform adjustments while checking the horizontality on the screen.

Further, it is possible to perform adjustments so as to fit to the patient's body with one touch by reading the previous detection value of the patient from the storage unit 112 and controlling and driving the motor 114 until the detection value is obtained. A change in the patient's body can be recognized by comparing the present state with the previously adjusted state.

This system can be applied to other adjustment mechanisms such as actuators for operating the chest mat 51 and the body mat 61 without being limited to the detection value obtained by the swing mechanism. That is, the sensors 113 are arranged in the movable portions of the treatment table 1 and the previous measurement values are stored. The operator may use various values indicating a change in the body in surgical operations without being limited to the distortion.

As illustrated in FIG. 1, the leg support 8 includes a leg mat 81 having a narrow rectangular shape in a plan view, and the leg mat 81 is attached to a flat leg plate 82. An upper end of a leg frame 84 of which the lower end can be adjusted to multiple length steps and is rotatably connected above a position close to the distal end of the connection frame 83 which is rotatably attached between the footstool 32 and the pair of body frames 31 is rotatably connected to the lower surface of the leg plate 82.

An upper end of a cylinder 85 as a holding unit of which the lower end is rotatably connected to an intermediate position of the connection frame 84 is rotatably connected to the lower surface of the leg plate 82. The height of the leg mat 81 can be adjusted in multiple steps (for example, three steps) by adjusting the rotation position (that is, the engagement position) of the lower end of the leg frame 84, and the adjusted height is held by the cylinder 85.

The cylinder 85 is configured so that the leg mat 81 can be rotated toward the footstool 32 by adjusting the length of the cylinder 85.

Further, a rotation shaft 86 having a disk shape in a side view is rotatably attached to the intermediate portion of the connection frame 83. The rotation shaft 86 is provided so as to be movable along a cam 87 attached to the machine table 2. When the body frame 31 is caused to stand up from the machine table 2 by the lift mechanism 21 from an approximately horizontal state and when the body frame 31 is caused to return from the standing-up state to the approximately horizontal state, the rotation shaft 86 moves along the cam 87 to allow the leg mat 81 and the footstool 32 are operated in synchronization with movement of the body frame 31.

Figure 10:
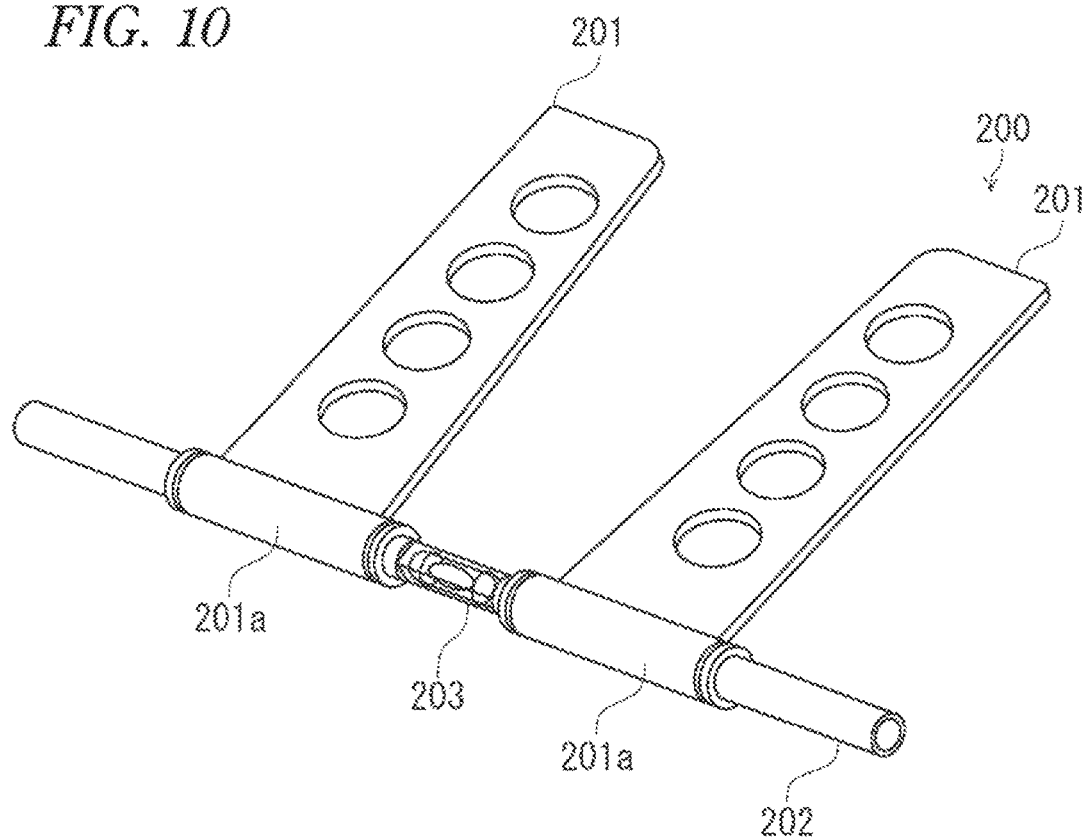
FIG. 10 is a perspective view of a body measurement level gauge used in a body measurement method according to the present invention.

Although the treatment table of the present invention has the above described configuration, it is further preferable to use a body measurement level gauge 200 illustrated in FIG. 10 together with the treatment table.

This level gauge 200 is a body measurement level gauge for measuring the distortion or the shift of the posture during treatments. As illustrated in FIGS. 1 and 2, the body measurement level gauge includes holders 201 which are flat plates which are erected in a state of being in contact with both left and right sides of the body of a patient in a state of lying on the belly and a horizontal rod 202 provided horizontally on upper edges 201a of the holders and used in a state of being placed on the upper surface of the patient's body.

A level 203 is attached to the horizontal rod 202 so that the horizontality of the horizontal rod can be checked. The body holders 201 are configured so that the interval thereof can be increased and decreased, and during the use, the patient's body (for example, the head, the chest, the belly, the waist, or the gluteal region) is located between the two holders. By reading the state of the level 203 in this state, it is possible to detect the distortion or the like of the body.

By using the body measurement level gauge 200 together with the treatment table 1 of the present invention, adjusting the swing unit so that the level 203 is horizontal, and measuring the swing position at that time, it is possible to measure the distortion of the patient's body easily and with high accuracy.

Moreover, it is possible to perform adjustment of the treatment table easily during treatments and to accurately understand the treatment effect by comparing with the previous adjustment position.

The sensor 113 may detect the swing positions of the head swing mechanism 48 and the waist swing mechanism 78 of the treatment table 1 in a state in which further adjustments are realized. An existing position detection sensor may be appropriately used as the sensor 113.

The detection value obtained by the sensor 113 is input to the CPU 110 and is stored in the storage unit 112 together with identification data of a patient, which is input separately. When adjustments are performed again after treatments and the detection values are compared, it is possible to understand the treatment effects quantitatively.

In the present invention, a body swing mechanism C-1 for allowing the body support 6 to swing may be provided similarly to the above head swing mechanism 48 and the waist swing mechanism 78. Since the body swing mechanism C-1 is realized by approximately the same structure as the waist swing mechanism 78, the illustration thereof is shown in FIG. 6 and FIG. 9. The body swing mechanism C-1 is configured to be able to swing in the width direction about a support point located at the central position in the width direction of the body mat 61 of the body support 6.

The body swing mechanism C-1 includes a pair of rails having an L-shaped cross-section bent in a concave arc shape and is attached to both ends in the longitudinal direction of the lower surface of the body swing plate in a state in which these rails face each other. These rails are formed to be bent in such a curvature that the support point is at the central position. A pair of cam followers which are cylindrical rollers is rotatably stored in the rails, and the cam followers are locked so as to be movable in the bending direction of these rails in relation to each other. The body swing plate can swing when a rotation handle connected via the cam follower and the interlocking shaft is rotated.

The body swing mechanism C-1 may include a motor for driving the interlocking shaft and may be electrically driven by electrically controlling the motor. An existing gear mechanism may be disposed between the motor and the interlocking shaft so that an operator can operate the rotation handle and perform motor-based driving.

When electric control is performed, an operation switch for performing an adjustment operation can be provided in an arbitrary place of the treatment table.

Moreover, an operator may perform an adjustment operation at another place with the aid of a link mechanism which uses gears, transmission rods, and the like and is connected to the interlocking shaft. For example, when a level for checking the horizontality of the treatment table is provided so that an operator can perform operations near the level, the operator can easily perform accurate leveling. Moreover, during surgical operations, it is preferable that the external occipital protuberance of the occipital region and the intergluteal cleft of the gluteal region are horizontal so that an adjustment operation can be performed while checking the horizontality of these regions.

In this manner, when the operator is allowed to perform operations near a position (for example, the position on the central line of the body such as above the head or below the legs) where it is easy to check the distortion or the like of the patient's body, it is possible to perform a highly accurate surgical operation.

The present invention is characterized in that the maximum swing range in the width direction of the head support about the central position in the swing motion of the width direction of the head support is selected from 30 mm to 40 mm in the horizontal direction, from 5 mm to 15 mm in a vertical direction (from the end of the head support), and from 10° to 15° in an oblique direction when the head support is moved to a maximum operable value in an arc form and the maximum swing range in the width direction of the body support and the waist support about the central position in the width direction of the body support and the waist support is selected from 30 mm to 40 mm in the horizontal direction, from 3 mm to 10 mm in the vertical direction, and from 10° to 15° in the oblique direction. That is, the head support, the body support, and the waist support are moved in an arc form up to the maximum points of the swing range.

In the present invention, in a configuration in which a rotation handle is provided in any one of the head swing mechanism 48, the body swing mechanism C-1, and the waist swing mechanism 78, it was found that the relation between a rotation operation of the rotation handle and the number of revolutions for the swing motion is very important in treatment accuracy.

As a result of repeated tests, the present inventors configured the treatment table such that the head support reaches the maximum swing range in the width direction when the rotation handle is rotated 15 to 30 revolutions and the body support and the waist support reaches the maximum swing range in the width direction when the rotation handle is rotated 10 to 20 revolutions. If the number of revolutions exceeds this range, although the adjustment accuracy increases, it is necessary to increase the number of revolutions and it is not possible to perform adjustments quickly. On the other hand, if the number of revolutions is smaller than this range, the head support, the body support, and the waist support may swing too easily and it is difficult to perform fine adjustments.

In the configuration in which the motor-based driving is performed, the operation time of the operation switch and the rotation angle preferably have such a relation that the motor is rotated within 0.5 to 1 revolution within the operation time of two seconds.

REFERENCE SIGNS LIST

1: Treatment table
4: Head support
5: Chest support
6: Body support
7: Waist support 48: Head swing mechanism
48d: Rotation handle
78: Waist swing mechanism
C-1: Body swing mechanism
78d: Rotation handle
9: Adjustment operation unit
90: Rotation handle
91: Rotation handle

The invention claimed is:

1. A treatment system comprising: at least a head support for supporting a head of a patient, a body support for supporting a body of the patient, a waist support for supporting a waist of the patient, and a body measurement level gauge provided on the body support for measuring a shift of a posture of the patient during treatment;

wherein the head support, the body support, and the waist support are connected sequentially; wherein the head support includes a first swing unit configured to swing the head support; the waist support includes a second swing unit configured to swing the waist support; and the body support includes a third swing unit configured to swing the body support; and wherein a plurality of adjustment operation units for adjusting the first swing unit, the second swing unit and the third swing unit are disposed in the treatment table; wherein one of the plurality of adjustment operation units is arranged on a front side of the head support and comprises a first rotation handle and a second rotation handle where the first rotation handle is linked to a first interlocking shaft of the head support and the second rotation handle is linked to a second interlocking shaft of the waist support; and wherein the body measurement level gauge includes a plurality of holders which are flat plates erected in a state of being in contact with both left and right sides of the body of the patient in a state of lying on a belly, a circular horizontal rod provided on a plurality of upper edges of the plurality of holders and placed on an upper surface of the body of the patient; and a level attached to the horizontal rod and adjusting one of the first swing unit, the second swing unit or the third swing unit so that the level is horizontal enables measurement of a swing position.

2. The treatment system according to claim 1, wherein an interval between the plurality of holders is adjustable.

3. The treatment system according to claim 1, wherein each of the flat plates comprise a plurality of apertures spaced along a length direction of the flat plates.

* * * * *